United States Patent
Mahony, III

[11] Patent Number: 5,282,802
[45] Date of Patent: Feb. 1, 1994

[54] METHOD OF SECURING A TENDON GRAFT WITH AN INTERFERENCE FIXATION SCREW

[76] Inventor: Thomas H. Mahony, III, 1730 Wood Ave., Colorado Springs, Colo. 80903

[21] Appl. No.: 746,965

[22] Filed: Aug. 19, 1991

Related U.S. Application Data

[63] Continuation-in-part of Ser. No. 476,252, Feb. 7, 1990, Pat. No. 5,062,843.

[51] Int. Cl.$^5$ .............................. A61F 5/04
[52] U.S. Cl. ........................ 606/72; 606/73; 606/60
[58] Field of Search ............. 606/60, 61, 62, 65, 606/72, 73, 76, 77, 104; 623/13, 16

[56] References Cited

U.S. PATENT DOCUMENTS

| | | |
|---|---|---|
| D. 245,516 | 8/1977 | Treace . |
| 2,570,465 | 10/1951 | Lundholm . |
| 4,539,981 | 9/1985 | Tunc ........................ 606/72 |
| 4,590,928 | 5/1986 | Hunt et al. ............... 623/13 |
| 4,716,893 | 1/1988 | Fischer et al. . |
| 4,834,752 | 5/1989 | Van Kampen . |
| 4,870,957 | 10/1989 | Goble et al. ............. 623/13 |
| 4,898,186 | 2/1990 | Ikada et al. . |
| 4,927,421 | 5/1990 | Goble et al. . |
| 5,080,665 | 1/1992 | Jarrett et al. ............ 606/219 |
| 5,084,051 | 1/1992 | Tömälä et al. .......... 606/76 |
| 5,108,399 | 4/1992 | Eitenmuller et al. .... 606/77 |
| 5,129,906 | 7/1992 | Ross et al. ............... 606/77 |

FOREIGN PATENT DOCUMENTS

| | | |
|---|---|---|
| 0260970 | 3/1988 | European Pat. Off. . |
| 3630863 | 3/1988 | Fed. Rep. of Germany . |
| 2622790 | 5/1989 | France . |
| 1375252 | 2/1988 | U.S.S.R. . |

OTHER PUBLICATIONS

Brochure, "M. Kurosaka Interference Fixation Screw System".

*Primary Examiner*—Robert A. Hafer
*Assistant Examiner*—Sam Rimell
*Attorney, Agent, or Firm*—Ice Miller Donadio & Ryan

[57] ABSTRACT

A method of securing a tendon graft in a ligament tunnel is described. The tendon graft is used to replace a ligament and has a length of tendon section with bone grafts attached to the tendon at each end. The method includes the step of providing an interference fixation screws made of material that is soft compared to bone. The fixation screws are cooled to a temperature to make them sufficiently rigid to track in a straight line when they are tightened in the ligament tunnel. Each bone graft is then secured in place in the ligament tunnel by inserting a fixation screw between each bone graft and the bone surrounding the ligament tunnel and tightening it therebetween. After each fixation screw is tightened, it has a portion extending beyond a respective entrance to the ligament tunnel which is then trimmed.

13 Claims, 1 Drawing Sheet

METHOD OF SECURING A TENDON GRAFT WITH AN INTERFERENCE FIXATION SCREW

This is a continuation-in-part application of copending application U.S. Ser. No. 07/476,252 now U.S. Pat. No. 5,062,843 for an Interference Fixation Screw With Integral Instrumentation, filed Feb. 7, 1990, invented by Thomas H. Mahony, III.

BACKGROUND AND SUMMARY OF THE INVENTION

This invention relates to ligament replacement, and more particularly to a method of securing tendon grafts used to replace ligaments in boney tunnels in the body with interference fixation screws.

Ligaments are connective tissue which join surfaces of bones together in a joint. They act to limit the motion of the bones of the joint relative to each other. Injuries to ligaments are not uncommon, particularly in patients who are active in sports. The anterior cruciate ligament of the human knee is especially susceptible to damage. Unfortunately, when an anterior cruciate ligament is damaged, it must often be replaced because it frequently never heals.

One method of replacing damaged ligaments is to use a section of tendon grafted from the knee cap or patella. A portion of tendon is excised from the patella. A portion of the bone (bone graft) to which each end of the tendon section is attached is excised with the tendon section. A hole or boney tunnel (ligament tunnel) is drilled through the femur and tibia. The tendon graft is inserted into the ligament tunnel in the femur and the ligament tunnel in the tibia and positioned so that it is centered in the two ligament tunnels. That is, an equal length of tendon graft is disposed in both the femur and in the tibia. A fixation screw is then tightened in the ligament tunnel between the bone graft and the side of the ligament tunnel in the bone to affix the bone graft in place. The tendon section is now appropriately tensioned and the bone graft attached to the other end of the tendon section is secured with a screw.

Heretofore, metal fixation screws have been used to affix the bone grafts in place. Such screws may be designed to be interference screws or may be standard bone screws with blunt threads. The interference screw is designed so that the screw will not cut into the bone graft or the side of the boney tunnel. Rather, when the screw is tightened in place, it forces the bone graft tightly against the side of the boney tunnel so that the bone graft is held in place by friction.

Metals screws do not always act as interference screws, even if designed as such. The threads of the metal screws can cut into the bone grafts and damage or even destroy the bone grafts. Further, if either the screw or the bone graft is slightly oversize, or the boney tunnel in which the bone graft is to be secured is slightly undersized, the lack of resiliency on the part of the threads of the metal screw can cause too much force to be exerted on the bone graft as the metal screw is tightened. This too can damage or destroy the bone graft. If this happens, the surgeon may be left without a bone graft to use to secure an end of the tendon graft in place. The tendon graft may then be useless. If this happens, either a new tendon graft must be taken from the patella or, if there is not sufficient tendon left in the patella to take a new graft, a different technique for replacing the damaged ligaments must be used such as an artificial ligament prosthesis. In most cases, however, using a natural part of the patient's body to replace the damaged ligament is preferable. Artificial ligaments have biocompatability and biodegradation problems which a tendon section from the patient's own patella does not have.

Another problem with the metal screws is that the length of tendon which can be grafted varies between individual patients. So too do the lengths of the ligament tunnels drilled in the tibia and femur. Consequently, when the tendon grafts are properly positioned in the ligament tunnels drilled in the femurs and tibias of patients, the distances the bone grafts are recessed in the ligament tunnels in the femurs and tibias vary from patient to patient. The screw which is used to affix the bone graft in place must be long enough to have adequate purchase against the bone graft but short enough so that any portion extending beyond the surface of the tibia or femur when the screw is tightened is minimized and preferably eliminated. Therefore, the surgeon must have available screws in several different lengths to be able to select ones having the proper length.

Finally, metal screws require separate instrumentation. In this context, "instrumentation" means a device which is used to facilitate the installation of the screw. Here, such instrumentation is some type of fastening device, such as a hex driver, which is used to tighten the screws. This requires that sterile instrumentation (fastening device) be available to the surgeon. This increases the number of sterile items that must be maintained in the operating room. It is an object of this invention to provide a fixation screw for securing in place in a ligament tunnel bone grafts of a tendon graft used to replace ligaments. The fixation screw is formed as an interference screw from a relatively soft material to prevent the threads of the screw from cutting into and damaging the bone grafts.

It is another object of this invention to provide a fixation screw where any excess projecting beyond the surface of the bone at which the ligament tunnel opens can be trimmed off after the fixation screw has been tightened.

It is yet another object of this invention to provide a fixation screw which has integral instrumentation used to tighten the screw in place and which is cut off when the excess screw material is trimmed after the screw has been tightened.

It is a further object of this invention to provide a method of implanting a fixation screw made from material that is soft compared to bone which maintains the positioning of the screw when it is being inserted.

An interference fixation screw in accordance with this invention is made of material that is soft compared to bone and is sufficiently long so that after it has been tightened in place in a ligament tunnel, it has a portion extending from the opening of the ligament tunnel. After insertion, the portion extending from the opening of the ligament tunnel is trimmed off. Preferably, the fixation screw is cooled, before it is inserted into the ligament tunnel. By cooling the fixation screw, it becomes more rigid so that the surgeon is better able to keep it properly positioned as it is tightened in the ligament tunnel between a bone graft of a tendon graft and the bone surrounding the ligament tunnel.

Additional features and advantages of the invention will become apparent to those skilled in the art upon consideration of the following detailed description of a preferred embodiment, exemplifying the best mode of The detailed description particularly refers to the accompanying figures in which.

Figure 1:
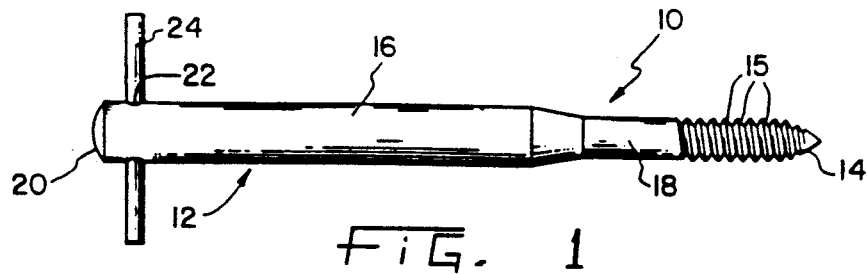
FIG. 1 is a perspective view of a fixation screw formed in accordance with this invention.

Referring to FIG. 1, a fixation screw 10 formed in accordance with the invention has a body 12 with a threaded end 14. Threaded end 14 has threads 15. Threaded end 14 is formed as an interference screw. Body 12 has a relatively thicker handle portion 16 connected to threaded end 14 by a necked down portion 18. At an end 20 opposite threaded end 14, handle portion 16 has a hole 22 extending transversely therethrough. A rod 24 can be inserted through hole 22 to facilitate tightening of fixation screw 10.

Body 12 of fixation screw 10 is fabricated as a single piece from a material which is relatively soft compared to bone. That is, the material from which body 12 is molded is sufficiently soft so that threads 15 of threaded end 14 of body 12 will yield when compressed against bone rather than cutting into the bone. Such material could be a bioabsorbable or biocompatible material. Illustratively, body 12 is machined from ultra-high molecular weight polyethylene which is a biocompatible plastic. Body 12 could also be molded such as from a biocompatible plastic.

By fabricating body 12 of fixation screw 10 from a relatively soft material, the threads 15 of threaded end 14 will not cut into the bone grafts when fixation screw 10 is tightened in place. Threads 15 will yield when compressed between the bone grafts and bone, as discussed in more detail below, rather than cutting into them.

Handle portion 16 comprises instrumentation which is used to tighten the fixation screw 10. That is, when fixation screw 10 is being installed, handle portion 16 is grasped by the surgeon and turned to tighten threaded end 14 as will be described in more detail below. By fabricating body 12 as a single piece, threaded end 14, handle portion 16, and necked down portion 18 are formed as an integral unit. Thus, fixation screw 10 includes integral instrumentation in that handle portion 16 and threaded end 14 are fabricated as integral pieces of body 12. Although rod 24 is shown as a separate piece in FIG. 1, it should be understood that it could be fabricated as part of fixation screw 10. For example, rod 24 and body 12 could be molded as a single piece.

Figure 2:
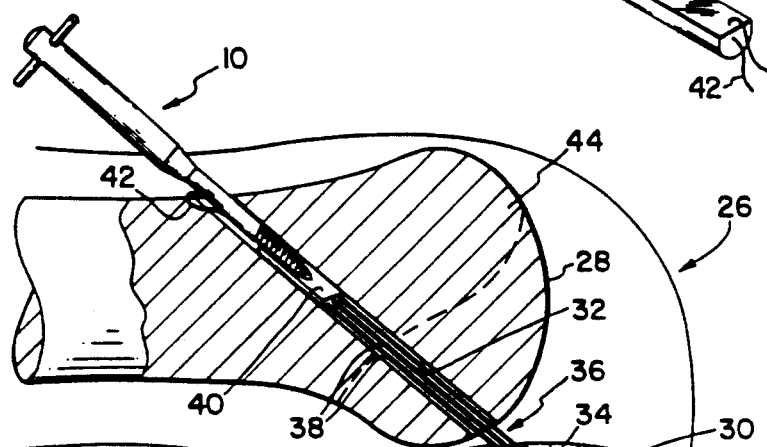
FIG. 2 is a perspective view of a knee joint in which a tendon graft used to replace the cruciate ligament of the knee has a bone graft at one end secured in place to the cruciate bone surrounding that end by the fixation screw of this invention.

Referring to FIG. 2, a knee joint 26 has a femur 28 and a tibia 30. Ligament tunnels 32, 34, are drilled through femur 28 and tibia 30, respectively, so that they are coaxial when the knee joint 26 is in flexion, as shown in FIG. 2. A tendon graft 36 is inserted in ligament tunnels 32, 34 and secured in place as described below to replace the cruciate ligament (not shown) of knee joint 26.

Figure 3:
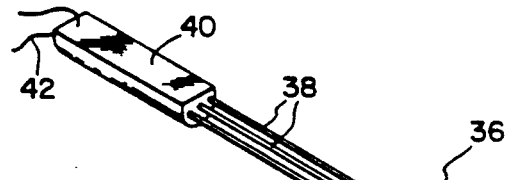
FIG. 3 is a perspective view of the tendon graft of FIG. 2.

Tendon graft 36 is taken from the patella (not shown) of knee joint 26. As best shown in FIG. 3, tendon graft 36 comprises a section of tendon 38 attached at each end to bone grafts 40. When taking tendon graft 36 from the patella, bone grafts 40, to which the ends of tendon section 38 are attached, are excised from the patella. Illustratively, bone grafts 40 are semi-cylindrical sections of bone sized to fit within ligament tunnels 32, 34. Typically, ligament tunnels 32, 34 would either be seven millimeters or ten millimeters in diameter. Similarly, the diameters or thicknesses of bone grafts 40 would be about seven or ten millimeters, respectively.

After tendon graft 36 is taken from the patella, it is inserted into ligament tunnels 32, 34. Before this is done, sutures 42 are usually placed in bone grafts 40 to hold bone grafts 40 in place ligament tunnels 32, 34 while fixation screws 10 are put in place. Tendon graft 36 is positioned in ligament tunnels 32, 34 so that approximately an equal amount of tendon section 38 is in ligament tunnel 32 in femur 28 and in ligament tunnel 34 in tibia 30.

As mentioned above, the length of tendon graft 36 varies from patient to patient. Also, the size of the femur and tibia, and thus the lengths of femur and tibia tunnels 32, 34, also varies from patient to patient. Consequently, when tendon graft 36 is properly positioned in ligament tunnels 32, 34, the bone grafts 40 will be recessed from the opening of ligament tunnel 32 at anterior surface 29 of femur 28 and from the opening of ligament tunnel 34 at an anterior surface 31 of tibia 30 distances which vary from patient to patient.

Figure 4:
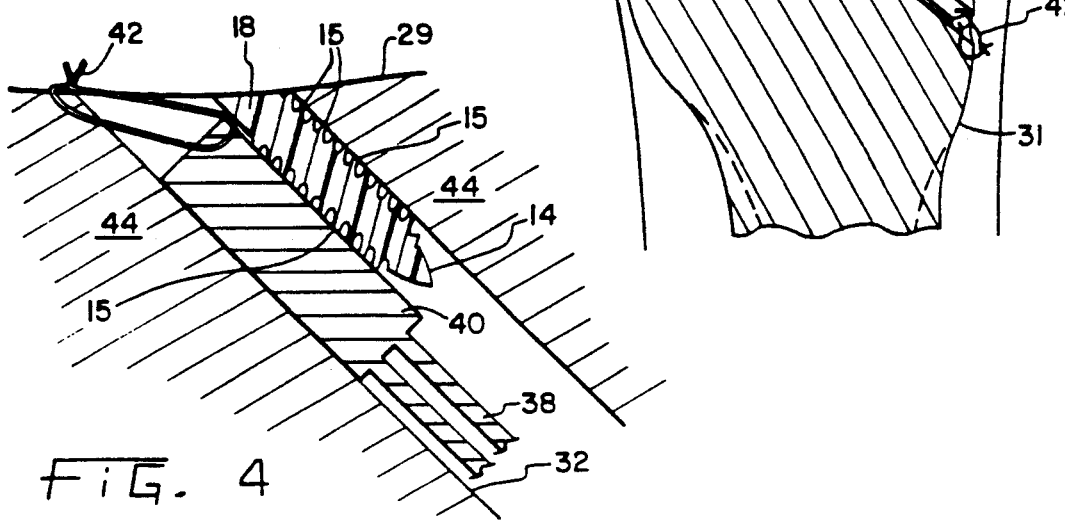
FIG. 4 is an exploded perspective view of FIG. 2 showing the bone graft in the ligament tunnel in the femur held in place by the fixation screw of this invention.

After tendon graft 36 is properly positioned in ligament tunnels 32, 34, the bone graft 40 in ligament tunnel 32 of femur 28 is sutured in place with sutures 42. A fixation screw 10 is then inserted into ligament tunnel 32 from anterior surface 29 of femur 28 and tightened. As shown in FIGS. 2 and 4, when fixation screw 10 is inserted in ligament tunnel 32, threaded end 14 of fixation screw 10 is placed between bone graft 40 and bone 44 which surrounds ligament tunnel 32. Handle portion 16 of fixation screw 10 is then twisted to turn fixation screw 10. As fixation screw 10 is turned, threaded end 14 will progressively advance between bone graft 40 and bone 44 and tighten therebetween. As threaded end 14 tightens between bone graft 40 and bone 44, it forces bone graft 40 against bone 44. Threads 15 of threaded end 14 will then begin to deform, since they are made from relatively soft material, as threaded end 14 forces bone graft 40 against bone 44 with ever increasing force. Consequently, threads 15 do not cut into bone graft 40 or bone 44, but deform.

After fixation screw 10 has been tightened in place, threaded end 14 will be disposed between bone graft 40 and bone 44 and forcing bone graft 40 against bone 44 with sufficient force so that bone graft 40 is maintained in place in ligament tunnel 32. As best seen in FIG. 4, threads 15 of threaded end 14 will be deformed or bent over after fixation screw 10 has been tightened. The deformation of threads 15 helps maintain bone graft 40 in place. If bone graft 40 begins to move, some of deformed threads 15 will have originally deformed in a direction to cause them to act against the movement of bone graft 40.

After fixation screw 10 has been tightened, the excess extending beyond the opening of ligament tunnel 32 at anterior surface 29 of femur 28 is trimmed off. This excess portion of fixation screw 10 can be cut off with an osteotome, chisel-like instrument, or the like. The trimmed end of fixation screw 10 will thus be flush with the anterior surface 29 of the femur at the opening of ligament tunnel 32 as shown in FIG. 4. Since the excess of fixation screw 10 can be trimmed after it has been tightened; only one length of fixation screw 10 is required.

Tendon graft 36 is now appropriately tensioned and the bone graft 40 in ligament tunnel 34 in tibia 30 is sutured in place. Another fixation screw 10 is then used to secure bone graft 40 in place in ligament tunnel 34 in similar fashion to that described above. The excess of fixation screw 10 extending beyond anterior surface 31 of tibia 30 at the opening of ligament tunnel 34 is then trimmed off. The trimmed end of fixation screw 10 holding the bone graft 40 in graft in ligament tunnel 34 will thus be flush with anterior surface 31 of tibia 30 at the opening of ligament tunnel 34.

In addition to securing tendon grafts in ligament tunnels in knees as just described, interference screw 10 can also be used to secure bone grafts, ligament grafts, or tendon grafts in boney tunnels. Although interference screw 10 has particular use in securing such grafts in boney tunnels in joints of humans, it can also be used to secure such grafts in boney tunnels in joints of animals or in any boney tunnel in an animal.

A problem that can occur with a fixation screw made of material soft compared with bone is that the fixation screw becomes less rigid as its temperature rises. This lessening of rigidity makes it more difficult for the surgeon to keep the fixation screw properly positioned as it is tightened in place in the ligament tunnel. Due to its flexibility, the screw does not track in a straight line as it is tightened but tends to wander from side to side. This problem can be solved or greatly reduced by cooling the fixation screw, such as fixation screw 10, before it is inserted in one of ligament tunnels 32, 34 to make it more rigid. Fixation screw 10 will thus be rigid when it is inserted in a ligament tunnel 32, 34 and will track in a straight line as it is tightened. This makes it easier for the surgeon to keep it properly positioned as it is tightened. Moreover, fixation screw 10 will expand slightly as it warms enhancing the interference fit between the bone grafts 40 and the bone surrounding ligament tunnels 32, 34. In the case of a fixation screw 10 made of ultra-high molecular weight polyethylene, cooling it to about forty degrees Fahrenheit makes it sufficiently rigid that it will track in a straight line as it is tightened in a ligament tunnel 32, 34.

Although the invention has been described in detail with reference to certain preferred embodiments, materials and specific examples, variations, and modifications exists within the scope and spirit of the invention as described and as defined in the following claims.

What is claimed is:

1. A method of affixing in place in a ligament tunnel a tendon graft used to replace a ligament, the tendon graft comprising a section of tendon having a bone graft at each end, comprising the steps of:
   (a) providing an interference fixation screw made of material that is soft compared to bone;
   (b) securing each bone graft in the ligament tunnel by tightening one of the fixation screws between each bone graft and the bone surrounding the ligament tunnel wherein the fixation screw has a portion extending beyond an entrance to the ligament tunnel after it has been tightened; and
   (c) trimming the portion of the fixation screw that extends beyond the entrance to the ligament tunnel.

2. The method of claim 1 and further including the step of cooling each fixation screw before it is inserted in the ligament tunnel to a temperature to make it sufficiently rigid so that it tracks in a straight line as it is tightened in place.

3. The method of claim 2 wherein the fixation screw is made from ultra-high molecular weight polyethylene and the step of cooling it comprises cooling it to approximately forty degrees Fahrenheit.

4. A method of implanting an interference fixation screw made of ultra high molecular weight polyethylene in a ligament tunnel in bone comprising the steps of:
   (a) cooling the fixation screw to about forty degrees Fahrenheit to make it sufficiently rigid so that is will track in a straight line as it is tightened; and
   (b) inserting the fixation into the ligament tunnel and tightening it.

5. A method of implanting an interference fixation screw made of material that is soft compared to bone in a ligament tunnel in bone comprising the steps of:
   (a) cooling the fixation screw to a temperature that makes it sufficiently rigid so that it will track in a straight line as it is tightened;
   (b) inserting the fixation screw into the ligament tunnel and tightening it to where it is tight and so that it has a portion extending beyond an entrance to the ligament tunnel; and
   (c) trimming the portion of the fixation screw that extends beyond the entrance of the ligament tunnel.

6. A method of affixing in place in a ligament tunnel a tendon graft used to replace a ligament, the tendon graft comprising a section of tendon having a bone graft at each end, comprising the steps of:
   (a) providing an interference fixation screw made of material that is soft compared to bone;
   (b) cooling each fixation screw before it is inserted into the ligament tunnel to a temperature that makes it sufficiently rigid to track in a straight line as it is tightened in the ligament tunnel;
   (c) securing each bone graft in the ligament tunnel by tightening one of the fixation screws between each bone graft and the bone surrounding the ligament tunnel wherein the fixation screw has a portion extending beyond an entrance to the ligament tunnel after it has been tightened; and
   (d) trimming the portion of the fixation screw that extends beyond the entrance to the ligament tunnel.

7. The method of claim 6 wherein the fixation screw is made from ultra-high molecular weight polyethylene and the step of cooling it comprises cooling it to approximately forty degrees Fahrenheit.

8. A method of affixing a tendon graft used to replace a ligament in place in tunnels formed in bones of a joint, the tendon graft comprising a length of tendon having bone grafts at each end, each bone of the joint having a ligament tunnel formed therein, comprising the steps of:
   (a) providing an interference fixation screw made of material that is soft compared to bone for each bone graft of the tendon graft to be secured in one of the ligament tunnels;
   (b) placing the tendon graft in the ligament tunnels with one of the bone grafts in each of the ligament tunnels;
   (c) securing each of the bone grafts in their respective ligament tunnels with one of the fixation screws by tightening each fixation screw between the bone graft it is securing in place and the bone surrounding the ligament tunnel in which the bone graft was placed wherein each fixation screw has a portion extending beyond an entrance of its respective ligament tunnel after it has been tightened; and (d) trimming the portion of each fixation screw that extends beyond the entrance to its respective ligament tunnel.

9. The method of claim 8 and further including the step of cooling each fixation screw prior to inserting it into a ligament tunnel to a temperature where it is sufficiently rigid so that it will track in a straight line when it is tightened.

10. The method of claim 9 wherein the step of providing the fixation screws comprises providing fixation screws made of ultra-high molecular weight polyethylene and the step of cooling the fixation screws comprises cooling them to approximately forty degrees Fahrenheit.

11. A method of affixing a tendon graft used to replace the anterior cruciate ligament in a knee in place in tunnels formed in the femur and the tibia of the knee, the tendon graft comprising a length of tendon having bone grafts at each end, comprising the steps of:

(a) providing an interference fixation screw made of material that is soft compared to bone for each bone graft of the tendon graft to be secured the ligament tunnels in the femur and the tibia;

(b) placing the tendon graft in the ligament tunnels with one of the bone grafts in each of the ligament tunnels in the femur and the tibia;

(c) securing each of the bone grafts in their respective ligament tunnels with one of the fixation screws by tightening each fixation screw between the bone graft it is securing in place and the bone surrounding the ligament tunnel in which the bone graft was placed wherein each fixation screw has a portion extending beyond an entrance of its respective ligament tunnel after it has been tightened; and (d) trimming the portion of each fixation screw that extends beyond the entrance to its respective ligament tunnel.

12. The method of claim 11 and further including the step of cooling each fixation screw prior to inserting it into a ligament tunnel to a temperature where it is sufficiently rigid so that it will track in a straight line when it is tightened.

13. The method of claim 12 wherein the step of providing the fixation screws comprises providing fixation screws made of ultra-high molecular weight polyethylene and the step of cooling the fixation screws comprises cooling them to approximately forty degrees Fahrenheit.

* * * * *